US00PP32871P2

(12) United States Plant Patent
Heuger

(10) Patent No.: US PP32,871 P2
(45) Date of Patent: Mar. 2, 2021

(54) ***HELLEBORUS* PLANT NAMED 'COSEH 6000'**

(50) Latin Name: ***Helleborus* x *ericsmithii* X *Helleborus* x *hybridus***
Varietal Denomination: COSEH 6000

(71) Applicant: Josef Heuger, Glandorf (DE)

(72) Inventor: Josef Heuger, Glandorf (DE)

( * ) Notice: Subject to any disclaimer, the term of this patent is extended or adjusted under 35 U.S.C. 154(b) by 0 days.

(21) Appl. No.: 16/873,648

(22) Filed: May 27, 2020

(51) Int. Cl.
*A01H 6/72* (2018.01)
*A01H 5/02* (2018.01)

(52) U.S. Cl.
USPC ..... Plt./439

(58) Field of Classification Search
USPC ..... Plt./439
See application file for complete search history.

(56) References Cited

PUBLICATIONS

PLUTO Plant Variety Database Sep. 15, 2020.*

* cited by examiner

*Primary Examiner* — Annette H Para
(74) *Attorney, Agent, or Firm* — C. Anne Whealy

(57) ABSTRACT

A new and distinct cultivar of *Helleborus* plant named 'COSEH 6000', characterized by its upright to outwardly spreading and mounded plant habit; moderately vigorous to vigorous growth habit; dark green-colored leaves; freely flowering habit; dark greyed purple-colored flowers; and good garden performance.

2 Drawing Sheets

Figure 1:
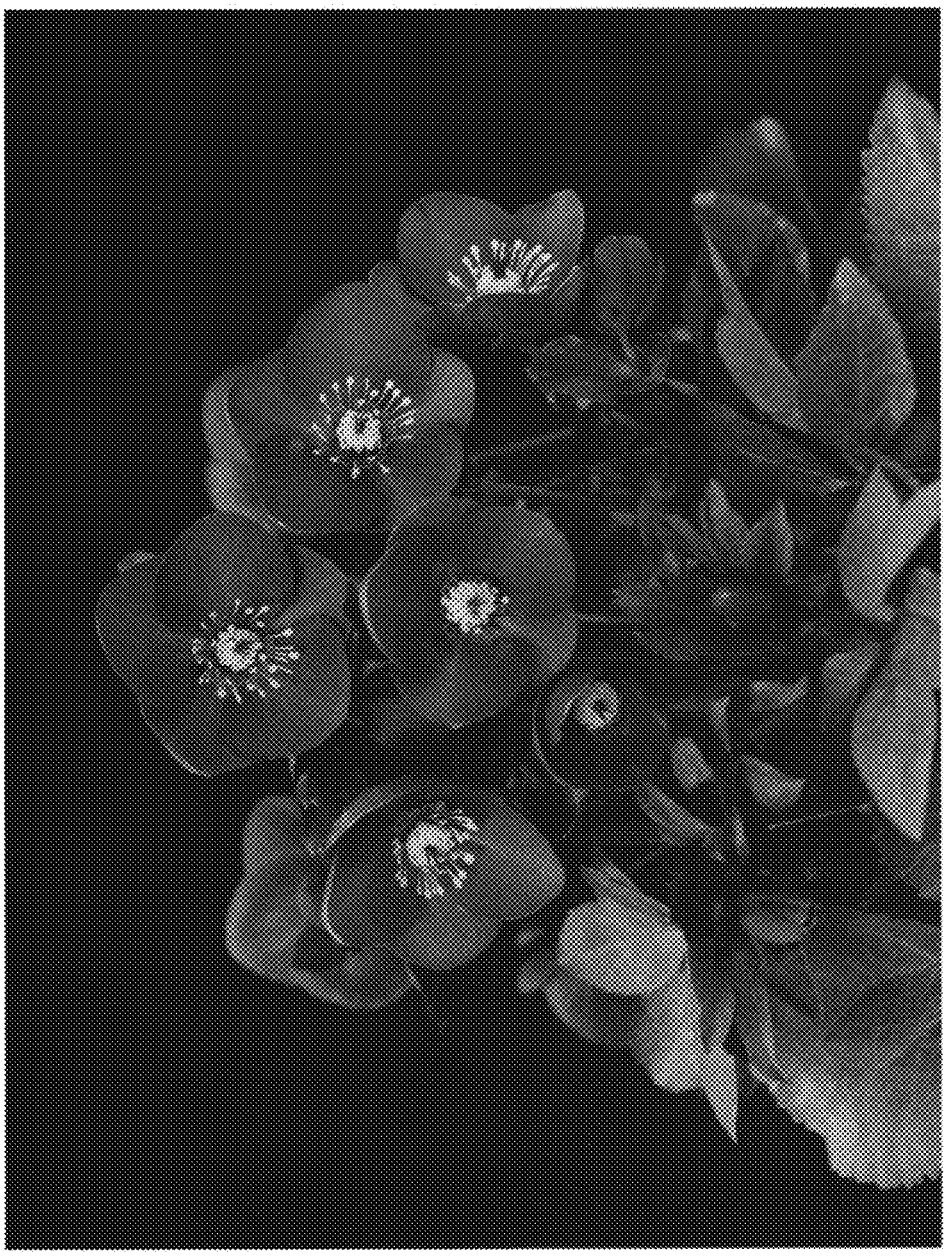

Botanical designation: *Helleborus* x *ericsmithii* X *Helleborus* x *hybridus*.
Cultivar denomination: 'COSEH 6000'.

CROSS-REFERENCED TO CLOSELY-RELATED APPLICATIONS

Title: *Helleborus* Plant Named 'COSEH 6100'
Inventor/Applicant: Josef Heuger
Plant patent application Ser. No. 16/873,647
Title: *Helleborus* Plant Named 'COSEH 6300'
Inventor/Applicant: Josef Heuger
Plant patent application Ser. No. 16/873,646
Title: *Helleborus* Plant Named 'COSEH 7900'
Inventor/Applicant: Josef Heuger
Plant patent application Ser. No. 16/873,651
Title: *Helleborus* Plant Named 'COSEH 8000'
Inventor/Applicant: Josef Heuger
Plant patent application Ser. No. 16/873,650

STATEMENT REGARDING PRIOR DISCLOSURES BY INVENTOR/APPLICANT

An European Community Plant Breeder's Rights application for the instant plant was filed by the Inventor/Applicant, Mr. Josef Heuger of Glandorf, Germany, on Jun. 6, 2019, application number 2019/1384. Foreign priority is not claimed to this application.

The Inventor/Applicant asserts that no publications nor advertisements relating to sales, offers for sale or public distribution occurred more than one year prior to the effective filing date of this application. Any information about the claimed plant would have been obtained from a direct or indirect disclosure from the Inventor or Applicant. Inventor/Applicant claims a prior art exemption under 35 U.S.C. 102(b)(1) for disclosure and/or sales prior to the filing date but less than one year prior to the effective filing date.

BACKGROUND OF THE INVENTION

The present invention relates to a new and distinct cultivar of *Helleborus* plant, botanically known as *Helleborus* x *ericsmithii* X *Helleborus* x *hybridus* and hereinafter referred to by the name 'COSEH 6000'.

The new *Helleborus* plant is a product of a planned breeding program conducted by the Inventor in Glandorf, Germany. The objective of the breeding program was to create new uniform *Helleborus* plants with unique and attractive plant habit, leaf and flower coloration and tolerance to biotic and abiotic stress.

The new *Helleborus* plant originated from a cross-pollination conducted by the Inventor in Glandorf, Germany in December, 2011 of a proprietary selection of *Helleborus* x *ericsmithii* identified as code number P840, not patented, as the female, or seed patent and an unnamed selection of *Helleborus* x *hybridus*, not patented, as the male, or pollen parent. The new *Helleborus* plant was discovered and selected by the Inventor as a single flowering plant from within the progeny of the stated cross-pollination grown in a controlled greenhouse environment in Glandorf, Germany in November, 2013.

Asexual reproduction of the new *Helleborus* plant by in vitro axillary meristem culture in a controlled environment in Glandorf, Germany since March, 2014 has shown that the unique features of this new *Helleborus* plant are stable and reproduced true to type in successive generations.

SUMMARY OF THE INVENTION

Plants of the new *Helleborus* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'COSEH 6000'. These characteristics in combination distinguish 'COSEH 6000' as a new and distinct *Helleborus* plant:

1. Upright to outwardly spreading and mounded plant habit.
2. Moderately vigorous to vigorous growth habit.
3. Dark green-colored leaves.
4. Freely flowering habit.
5. Dark greyed purple-colored flowers.
6. Good garden performance.

Plants of the new *Helleborus* differ from plants of the female parent selection in the following characteristics:

1. Plants of the new *Helleborus* are more compact than and not as vigorous as plants of the female parent selection.
2. Flowers of plants of the new *Helleborus* are darker greyed purple in color than flowers of plants of the female parent selection.

Plants of the new *Helleborus* differ from plants of the male parent selection in the following characteristics:

1. Leaves of plants of the new *Helleborus* are darker green in color than leaves of plants of the male parent selection.
2. Leaf venation of plants of the new *Helleborus* is more visible than leaf venation of plants of the male parent selection.

Plants of the new *Helleborus* can be compared to plants of *Helleborus* x *ericsmithii* X *Helleborus* x *hybridus* 'COSEH 6100', disclosed in a U.S. Plant Patent application filed concurrently. Plants of the new *Helleborus* differ primarily from plants of 'COSEH 6100' in flower color as plants of the new *Helleborus* have dark greyed purple-colored flowers whereas plants of 'COSEH 6100' have greyed purple to greyed red purple-colored flowers.

Plants of the new *Helleborus* can be compared to plants of *Helleborus* x *ericsmithii* X *Helleborus* x *hybridus* 'COSEH 6300', disclosed in a U.S. Plant Patent application filed concurrently. Plants of the new *Helleborus* differ primarily from plants of 'COSEH 6300' in flower color as plants of the new *Helleborus* have dark greyed purple-colored flowers whereas plants of 'COSEH 6300' have yellow green to greenish white-colored flowers with red purple to greyed purple-colored margins.

Plants of the new *Helleborus* can be compared to plants of *Helleborus* x *ericsmithii* X *Helleborus* x *hybridus* 'COSEH 7900', disclosed in a U.S. Plant Patent application filed concurrently. Plants of the new *Helleborus* differ primarily from plants of 'COSEH 7900' in flower color as plants of the new *Helleborus* have darker greyed purple-colored flowers than plants of 'COSEH 7900'.

Plants of the new *Helleborus* can be compared to plants of *Helleborus* x *ericsmithii* X *Helleborus* x *hybridus* 'COSEH 8000', disclosed in a U.S. Plant Patent application filed concurrently. Plants of the new *Helleborus* differ primarily from plants of 'COSEH 8000' in flower color as plants of the new *Helleborus* have dark greyed purple-colored flowers whereas plants of 'COSEH 8000' have greyed purple to dark purple-colored flowers.

Plants of the new *Helleborus* can also be compared to plants of *Helleborus* x *ericsmithii* X *Helleborus* x *hybridus* 'LEM 100', disclosed in U.S. Plant Pat. No. 25,646. In side-by-side comparisons, plants of the new *Helleborus* differ primarily from plants of 'LEM 100' in the following characteristics:

1. Plants of the new *Helleborus* are more vigorous than plants of 'LEM 100'.
2. Plants of the new *Helleborus* have smaller flowers than plants of 'LEM 100'.

BRIEF DESCRIPTION OF THE PHOTOGRAPHS

The accompanying colored photographs illustrate the overall appearance of the new *Helleborus* plant showing the colors as true as it is reasonably possible to obtain in colored reproductions of this type. Colors in the photographs may differ slightly from the color values cited in the detailed botanical description which accurately describe the colors of the new *Helleborus* plant.

The photograph on the first sheet (FIG. 1 of 2) is a side perspective view of a typical flowering plant of 'COSEH 6000' grown in a container.

Figure 2:
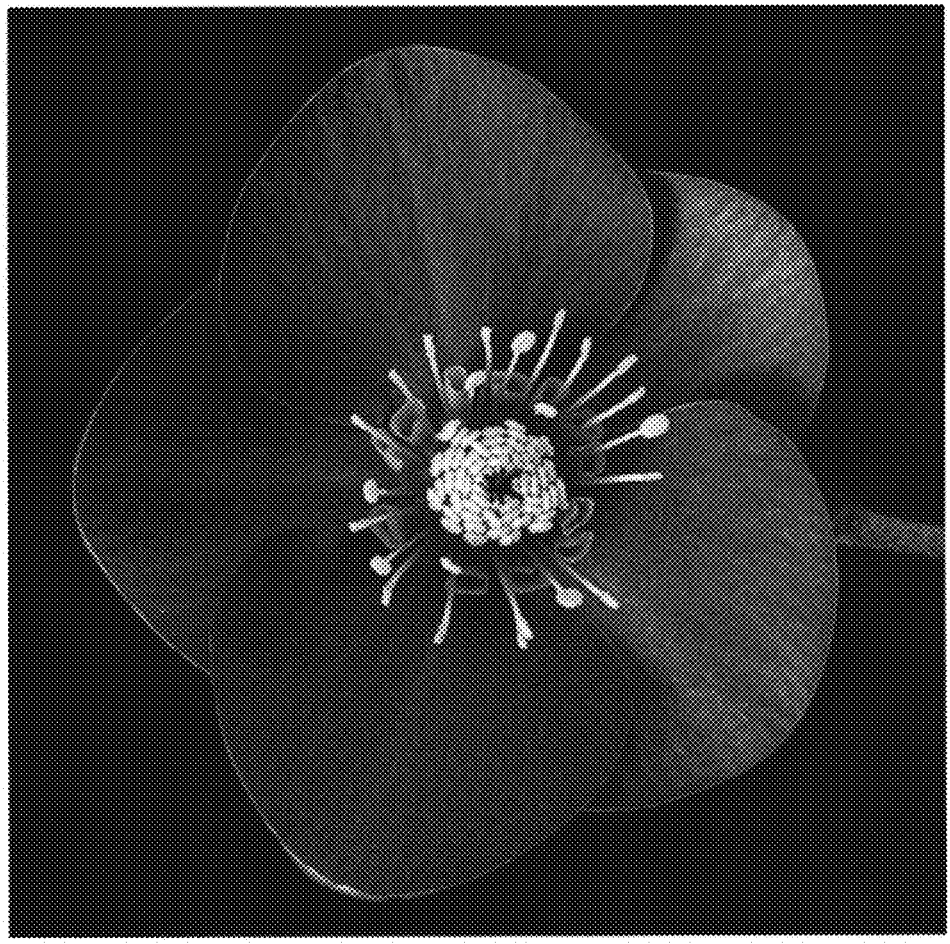

The photograph on the second sheet (FIG. 2 of 2) is a close-up view of a typical flower of 'COSEH 6000'.

DETAILED BOTANICAL DESCRIPTION

The aforementioned photographs and following observations, measurements and values describe plants grown during March in 17-cm containers in a glass-covered greenhouse in Glandorf, Germany and under cultural practices typical of commercial *Helleborus* production. During the production of the plants, day temperatures ranged from 12° C. to 32° C. and night temperatures ranged from 5° C. to 12° C. Plants were four months old when the photographs and the description were taken. In the following description, color references are made to The Royal Horticultural Society Colour Chart, 2015 Edition, except where general terms of ordinary dictionary significance are used.

Botanical classification: *Helleborus* x *ericsmithii* X *Helleborus* x *hybridus* 'COSEH 6000'.

Parentage:

*Female, or seed, parent.*—Proprietary selection of *Helleborus* x *ericsmithii* disclosed as code number P840, not patented.

*Male, or pollen, parent.*—Unnamed selection of *Helleborus* x *hybridus*, not patented.

Propagation:

*Type.*—In vitro axillary meristem culture.

*Time to initiate roots, winter.*—About 55 days at temperatures about 12° C.

*Time to produce a rooted young plant, winter.*—About 170 days at temperatures ranging from 4° C. to 15° C.

*Root description.*—Thick to thin, fleshy; typically white to brown in color, actual color of the roots is dependent on substrate composition, water quality, fertilizer type and formulation, substrate temperature and physiological age of roots.

*Rooting habit.*—Low branching; sparse.

Plant description:

*Plant and growth habit.*—Herbaceous perennial; upright and mounding plant habit with flowers held within and above the foliar plane; plant shape, roughly flattened globular; moderately vigorous to vigorous growth habit and moderate to rapid growth rate.

*Plant height, soil level to top of foliar plane*.—About 28 cm.

*Plant height, soil level to top of flowers*.—About 47.3 cm.

*Plant diameter* (*area of spread*).—About 66.5 cm.

Leaf description:

*Arrangement*.—Leaves arranged in a basal rosette; leaves palmately compound with typically five leaflets per leaf.

*Leaf length*.—About 17.3 cm.

*Leaf width*.—About 19.6 cm.

*Leaflet length*.—About 11.6 cm.

*Leaflet width*.—About 7.1 cm.

*Leaf shape*.—Palmate; reniform to orbicular in outline.

*Leaflet shape*.—Ovate to elliptic and obovate.

*Leaflet apex*.—Acute.

*Leaflet base*.—Attenuate.

*Leaflet margin*.—Serrate; coarsely undulate.

*Leaflet texture and luster, upper and lower surfaces*.—Smooth, glabrous; leathery; slightly glossy.

*Leaflet venation pattern*.—Pinnate.

*Leaflet color*.—Developing leaflets, upper surface: Close to NN137C; midvein proximally, tinged with close to N186C. Developing leaflets, lower surface: Slightly darker than N186C. Fully developed leaflets, upper surface: Slightly darker than between 147A and N189A; venation, close to 143B and proximally, close to 187A. Fully developed leaflets, lower surface: Close to 148B moderately tinged with close to N186C; venation, close to 187A.

*Petioles*.—Length: About 17.7 cm. Diameter: About 7 mm to 8 mm. Strength: Strong. Texture and luster, upper and lower surfaces: Smooth, glabrous; moderately glossy. Color, upper and lower surfaces: Close to 147D heavily covered with fine dots, close to 187A to 187B.

Flower description:

*Flower shape and habit*.—Rotate flowers; flowers moderately cupped; arranged in panicles; freely flowering habit with about seven flowers per inflorescence and about 77 flowers developing per plant; flowers face mostly outwardly to slightly nodding.

*Fragrance*.—None detected.

*Natural flowering season*.—Plants begin flowering about ten months after planting; plants flower naturally from winter into the late winter in Germany.

*Flower longevity on the plant*.—About ten days; sepals persistent, other flower parts are not persistent.

*Flower buds*.—Length: About 2.3 cm. Diameter: About 1.6 cm. Shape: Broadly ovate. Texture and luster: Smooth, glabrous; slightly glossy. Color: Close to between 59B and N77B; venation, close to 187B.

*Inflorescence height* (*including peduncle*).—About 48 cm.

*Inflorescence diameter*.—About 22.6 cm.

*Flower diameter*.—About 6.2 cm by 6.2 cm.

*Flower depth* (*height*).—About 2.3 cm.

*Petals*.—All petals are transformed into nectaries.

*Sepals*.—Quantity and arrangement: About five, arranged in a single whorl. Length: About 3.5 cm. Width: About 3.2 cm. Shape: Broadly ovate, slightly concave. Apex: Obtuse. Base: Truncate to broadly cuneate. Margin: Entire; not undulate. Texture and luster, upper and lower surfaces: Smooth, glabrous; matte. Color: When opening, upper surface: Close to 183D; proximally, flushed with close to lighter than 148D; venation, similar to lamina. When opening, lower surface: Close to between 59A and 183B; proximally, slightly tinged with close to lighter than 148D; venation, close to 187B. Fully opened, upper surface: Close to 185D moderately tinged with close to lighter than 177D; with development, color becoming closer to N186C moderately tinged with close to 200C; venation, similar to lamina. Fully opened, lower surface: Close to between 59A and 187B; with development, color becoming closer to N186C fading lighter towards the base to close to N186D; venation, close to 187A.

*Flower bracts*.—Quantity per flower: Typically one or two. Length: About 4.2 cm. Width: About 2.8 cm. Shape: Ovate. Apex: Acute. Base: Truncate. Margin: Sparsely and finely serrate; slightly undulate. Color, upper surface: Slightly darker than between NN137A and 147A; venation, similar to lamina. Color, lower surface: Slightly darker than N186C; venation, similar to lamina.

*Peduncles*.—Length: About 40.5 cm. Diameter: About 1 cm. Aspect: About 20° from vertical. Strength: Strong. Texture and luster: Smooth, glabrous; moderately glossy. Color: Close to 150D, heavily covered with fine dots, close to 187B to 187C.

*Pedicels*.—Length: About 2.2 cm. Diameter: About 2.5 mm to 3 mm. Aspect: About 10° to 30° from peduncle axis. Strength: Moderately strong. Texture and luster: Smooth, glabrous; moderately glossy. Color: Close to 183A.

*Reproductive organs*.—Stamens: Quantity per flower: About 60. Filament length: About 1.5 cm. Filament color: Close to 157D to lighter than 157D; proximally, close to 75C. Anther shape: Double and broadly reniform; basifixed. Anther size: About 2.5 mm by 2 mm. Anther color: Close to 150C. Pollen amount: Scarce to moderate. Pollen color: Close to 4D to lighter than 4D. Pistils: Quantity per flower: About five to eight. Pistil length: About 1.2 cm. Stigma diameter: About 0.3 mm. Stigma shape: Club-shaped. Stigma color: Close to 155A. Style length: About 1.2 cm. Style color: Close to 186A. Ovary color: Close to N186D. Nectaries (transformed petals): Quantity per flower: About eleven. Length: About 9 mm. Diameter: About 5 mm. Shape: Tubular, flattened. Texture and luster, inner and outer surfaces: Smooth, glabrous; slightly glossy. Color, immature, inner surface: Close to 151D. Color, immature, outer surface: Close to 151D; spot at base, close to 152C. Color, mature, inner surface: Close to 151B; proximally, close to 146D; with development, proximally becoming closer to 144B. Color, mature, outer surface: Close to 151B; proximally, close to 146D; spot at base, close to 152C; with development, proximally becoming closer to 144B.

*Seeds and fruits*.—To date, seed and fruit development have not been observed on plants of the new *Helleborus*.

Garden performance: Plants of the new *Helleborus* have been observed to have good garden performance and to tolerate rain, wind, high temperatures about 35° C. and to be suitable for USDA Hardiness Zones 5 through 9.

Pathogen & pest resistance: To date, plants of the new *Helleborus* have not been observed to be resistant to pathogens and pests common to *Helleborus* plants.

It is claimed:

1. A new and distinct *Helleborus* plant named 'COSEH 6000' as illustrated and described.

* * * * *